US00PP11588P

United States Patent [19]

Boeder

[11] Patent Number: Plant 11,588

[45] Date of Patent: Oct. 24, 2000

[54] CHRYSANTHEMUM PLANT NAMED 'MARI TIME'

[75] Inventor: Mark Boeder, West Wittering, United Kingdom

[73] Assignee: Cleangro Limited, United Kingdom

[21] Appl. No.: 09/160,118

[22] Filed: Sep. 24, 1998

[51] Int. Cl.[7] ..... A01H 5/00

[52] U.S. Cl. ..... Plt./295

[58] Field of Search ..... Plt./295

*Primary Examiner*—Howard J. Locker
*Attorney, Agent, or Firm*—Christie, Parker & Hale, LLP

[57] ABSTRACT

A new plant variety of chrysanthemum producing large, yellow daisy-type flowers having a yellow-green center.

1 Drawing Sheet

BACKGROUND OF THE INVENTION

The present invention is directed to a new and distinct variety of chrysanthemum botanically classified as *Dendranthema grandiflora*. The varietal denomination of the new chrysanthemum is 'Mari Time'.

The female parent of the new variety is the variety known as 'Miramar' (U.S. Plant Pat. No. 7,469) and the male parent is an undistributed variety identified as P12-90. The new variety has been asexually reproduced by vegetative cuttings in Ventura County, Calif. and the distinguishing characteristics are retained through successive generations of asexual reproduction.

SUMMARY OF THE INVENTION

'Mari Time' produces large, yellow daisy-type flowers with a green center on a plant suitable for pot plant production.

COMPARISON WITH PARENT

'Mari Time' differs from the female plant in having many more ray florets and an earlier blooming time. In side by side comparisons of plants grown under the same conditions the new variety blooms about five days earlier.

BRIEF DESCRIPTION OF ILLUSTRATION

The accompanying photograph shows typical specimens of the plant and flowers of the new variety with colors being as nearly true as possible with illustrations of this type.

DESCRIPTION OF THE PLANT

The following description of the new variety is of specimens grown in a greenhouse in Ventura County, Calif. in the month of April. 'Mari Time' has not been observed under all possible environmental conditions. The phenotype may vary with variations in the environment such as temperature, light intensity, day length and cultural conditions. The color designations herein are from The Royal Horticultural Society Colour Chart except where general terms are used.

To produce a commercial product the plants may be pinched once with center buds removed about ten days after planting rooted cuttings. It has been observed that longevity of individual blooms of 'Mari Time' is about 24 days and the response time is about 8 weeks. One application of growth retardant B9 at 2500 ppm is desirable. The following description is of plants given this application of growth regardant. Useful growing conditions include night temperatures of about 18°–20° C, day temperatures of about 20°–30° C.

Plant:
- *Habit.*—Upright herbaceous.
- *Height.*—About 28 cm.
- *Number of breaks from pinch.*—About 3 to 4.
- *Length of lateral branches.*—About 23 cm.
- *Stem color.*—Near 138A.

Foliage:
- *Leaf arrangement.*—Alternate.
- *Number of leaves per lateral branch.*—About 13.
- *Leaf size.*—Length: About 8 cm. Width: About 4.8 cm.
- *Leaf shape.*—Ovate.
- *Attachment.*—Petioled.
- *Leaf apex.*—Obtuse.
- *Base.*—Tapered.
- *Margin.*—Palmately lobed, serrate.
- *Aspect.*—Slightly undulate.
- *Surface.*—Top: Lightly pubescent. Bottom: pubescent.
- *Venation color.*—Upperside: Near 138B. Underside: Near 146C.
- *Petiole.*—Length: About 1.8 cm. Color: Near 146C.
- *Color.*—Mature leaf: Top: Near 137A. Bottom: Near 138A. Young leaf: Top: Near 137B. Bottom: Near 137C.

Bloom:
- *Inflorescence form.*—Cyme, sub-erect.
- *Bloom type.*—Daisy.
- *Number of blooms per branch.*—About 5 to 6.
- *Diameter of fully expanded bloom.*—About 10 cm.
- *Depth of fully expanded bloom.*—About 3.3 cm.
- *Diameter of disc.*—About 2 cm.
- *Sepal number.*—About 30. Color: Near 137C. Length: About 1 cm. Width: About 0.5 cm.
- *Peduncle.*—Length: Terminal: About 5.1 cm. Lateral: About 7.8 cm.
- *Habit.*—Straight, strong.
- *Surface.*—Highly pubescent.
- *Color.*—Near 138B.
- *Flower Bud* (*when just showing color*).—Color: Near 4A. Diameter: Near 1.2 cm. Height: About 0.8 cm.
- *Ray florets.*—Number per flower: About 70. Texture: Shiny. Shape: Oblanceolate. Apex: 3 obtuse irregular lobes. Margin: Entire. Aspect: Slightly recurved. Length: About 5 cm. Width: About 1.4 cm.
- *Disc florets.*—Number per flower: About 210. Texture: Shiny. Shape: Cylindric. Length: About 0.7 cm. Width: About 0.2 cm.

*Fragrance.*—Moderate.

Flower color:

*General flower description.*—Bright yellow daisy with a yellow-green disc.

*Ray florets, top side.*—Immature: Near 7C. Mature: Near 9A. Fading: Near 9B.

*Ray floret, under side.*—Immature: Near 8A. Mature: Near 12B. Fading: Near 12B.

*Disc florets.*—Immature: Near 144B. Mature: Near 1B. Fading: Near 7A.

*Changes as the flower ages.*—Yellow-green center gradually turns yellow. Flower color fades just slightly. Outer ray florets become very undulate.

Reproductive organs:

*Ray florets.*—Pistillate. Stigma shape: 2 branched. Stigma color: Near 7A. Style length: About 0.5 cm. Style color: Near 1D.

*Disc florets.*—Stigma shape: Linear. Stigma color: Near 5A. Style length: About 0.35 cm. Style color: Near 154D. Stamen number: About 5. Anther length: About 0.3 cm. Pollen color: Near 15A. Pollen quantity: Moderate.

What is claimed is:

1. A new and distinct chrysanthemum plant of the variety substantially as herein shown and described.

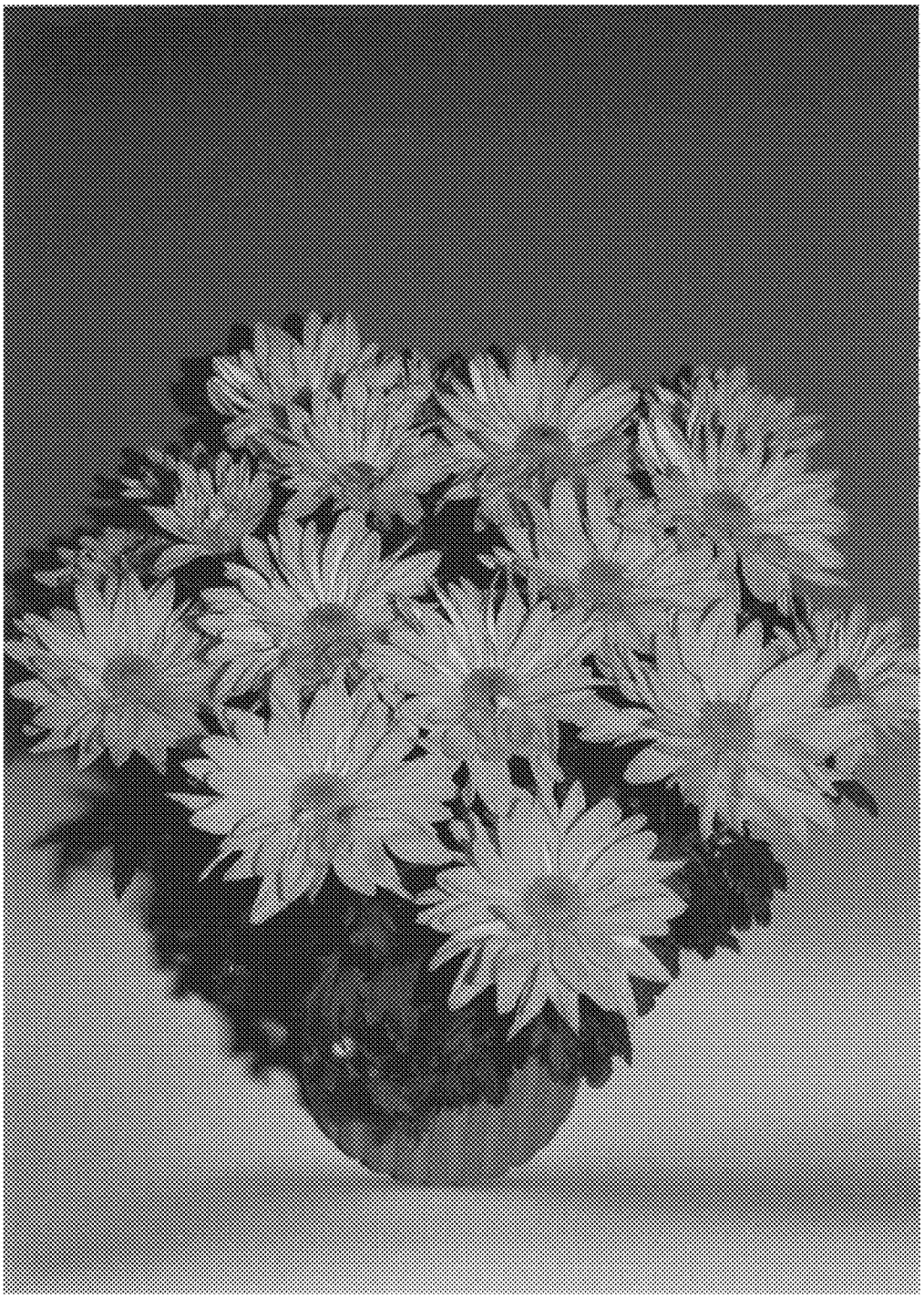

* * * * *